United States Patent [19]

Crenshaw et al.

[11] 4,157,340

[45] Jun. 5, 1979

[54] N,N'-[BIS(N-CYANOGUANYL)]CYSTAMINE DERIVATIVES

[75] Inventors: Ronnie R. Crenshaw, Dewitt, N.Y.; Gerry Kavadias, St. Lambert; Roger F. Saintonge, Montreal, both of Canada

[73] Assignee: Bristol-Meyers Company, New York, N.Y.

[21] Appl. No.: 919,597

[22] Filed: Jun. 27, 1978

[51] Int. Cl.² ........................................ C07C 125/08
[52] U.S. Cl. .............................................. 260/551 C
[58] Field of Search ....... 260/453 RW, 551 C, 564 E, 260/564 H

[56] References Cited

U.S. PATENT DOCUMENTS 3,894,151  7/1975  Black et al. .................. 424/250 X
3,950,333  4/1976  Durant et al. ............... 260/302 R X

FOREIGN PATENT DOCUMENTS 2654515  6/1977  Fed. Rep. of Germany ....... 260/564 E

OTHER PUBLICATIONS

Khym et al., JACS 79, 5663–5666 (1957).

*Primary Examiner*—Thomas A. Waltz
*Attorney, Agent, or Firm*—Richard R. Lloyd

[57] ABSTRACT

Novel compounds of the formula

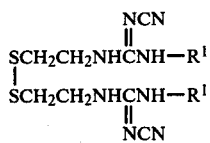

IV wherein each $R^1$ is the same and is a straight or branched chain alkynyl group containing from 3 to 9 carbon atoms, inclusive, which are useful intermediates in the preparation of anti-ulcer agents, are prepared by reacting cystamine (VI) with an N-cyano-N'-alkynyl-S-methylisothiourea of the formula

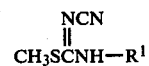

VII in which $R^1$ is as defined above.

10 Claims, No Drawings

N,N'-[BIS(N-CYANOGUANYL)]CYSTAMINE DERIVATIVES

SUMMARY OF THE INVENTION

This application relates to certain novel N,N'-bis[(N-cyano-N'-alkynyl)methanimidamidyl]cystamines of the formula

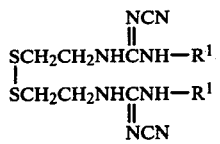

wherein each $R^1$ is the same and is a straight or branched chain alkynyl group containing from 3 to 9 carbon atoms, inclusive, which are useful as intermediates in the preparation of anti-ulcer agents of the formula

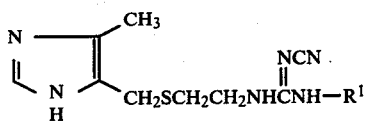

wherein $R^1$ is as defined above.

BACKGROUND AND PRIOR ART

The clinical objective in treatment of peptic ulcer disease is to decrease gastric acid secretion, based on the principle "no acid, no ulcer". Traditional peptic ulcer disease therapy involves control of diet and the use of antacids and anticholinergics.

There is evidence indicating that histamine may be the final common pathway for stimulation of gastric secretion. This effect of histamine is mediated via $H_2$ receptors and is not inhibited by the classical antihistamines, which are $H_1$ receptor blockers. A number of specific $H_2$ receptor blocking agents ($H_2$ receptor antagonists) are now known. These compounds inhibit basal acid secretion, as well as secretion by other known gastric acid stimulants, and are useful in the treatment of peptic ulcers.

Burimamide (Va) was the first clinically effective $H_2$ receptor antagonist.

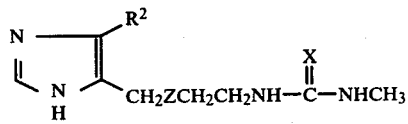

Va; $R^2$=H, Z=$CH_2$, X=S—Burimamide
b; $R^2$=$CH_3$, Z=S, X=S—Metiamide
c; $R^2$=$CH_3$, Z=S, X=NCN—Cimetidine It inhibits gastric secretion in animals and man, but oral absorption is poor. Metiamide (Vb), a subsequently evaluated $H_2$ antagonist, is more potent than burimamide and is orally active in man. Clinical utility was limited, however, owing to toxicity (agranulocytosis). Cimetidine (Vc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200–300 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et al., Federation Proceedings, 35, 1924 (1976), in Drugs of the Future, 1, 13 (1976), and in references cited therein.

Our colleagues' co-pending application Ser. No. 848,959, filed Nov. 7, 1977, now U.S. Pat. No. 4,112,234, (the disclosure of which is incorporated herein by reference) describes and claims novel histamine $H_2$ receptor antagonists of the formula

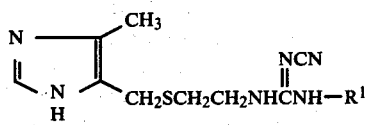

wherein $R^1$ is a straight or branched chain alkynyl group containing from 3 to 9 carbon atoms, inclusive, and nontoxic, pharmaceutically acceptable salts thereof, which are effective inhibitors of gastric secretion in animals, including man, and which are useful in the treatment of peptic ulcer disease.

Our colleagues' co-pending application Ser. No. 906,901 filed May 18, 1978 (the disclosure of which is incorporated herein by reference) discloses and claims novel intermediates of the formula

wherein $R^1$ is as described above, and a novel process for the preparation of anti-ulcer compounds of Formula I by reacting a compound of Formula III with a compound of the formula

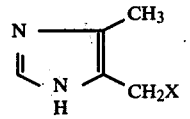

wherein X is a conventional leaving group, and wherein the compound of Formula II preferably is in the form of an acid addition salt.

Cystamine (VI) is a known compound, being described

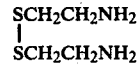

for example, on page 363 of The Merck Index, ninth edition (1976), as compound 2775.

Pantethine, a derivative or cystamine having the formula

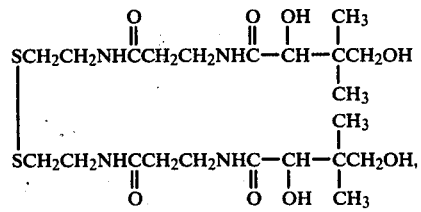

is described in The Merck Index, ninth edition (1976) as compound 6817.

The compound N,N'-bis(p-tolylsulfonylcarbamoyl)-cystamine having the formula

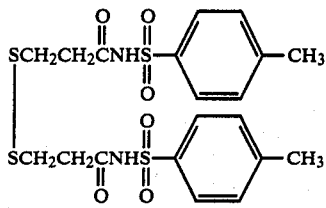

is listed in the Alfred Bader Chemicals Library of Rare Chemicals, Aldrich Chemical Company, Inc. (1971) by structure on page 114 and by name on page 275.

The Journal of The American Chemical Society, 79, 5663–6 (1957) discloses guanidinoethyldisulfide [N,N'-bis(guanyl)cystamine], having the formula

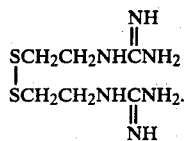

Complete Disclosure

In its broadest aspect, this invention relates to novel N,N'-bis[(N-cyano-N'-alkynyl)methanimidamidyl]cystamines of the formula

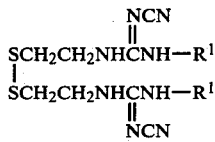

wherein each $R^1$ is the same and is a straight or branched chain alkynyl group containing from 3 to 9 carbon atoms, inclusive, and acid addition salts thereof.

In a preferred embodiment the compounds of Formula IV have the structure

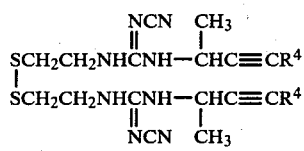

wherein each $R^4$ is the same and is hydrogen or methyl, or an acid addition salt thereof.

In another preferred embodiment the compounds of Formula IV have the structure

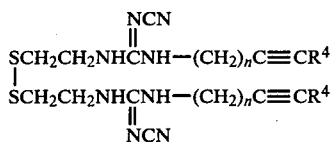

wherein each $R^4$ is the same and is hydrogen or methyl, and n is an integer of from 1 to 6 inclusive, or an acid addition salt thereof.

In yet another preferred embodiment the compounds of Formula IV have the structure

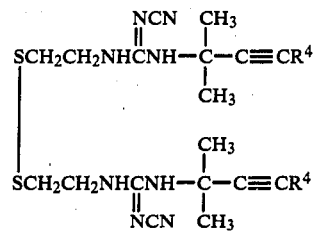

wherein each $R^4$ is the same and is hydrogen or methyl, or an acid addition salt thereof.

In a more preferred embodiment the compound of Formula IV is N,N'-bis[{N-cyano-N'-(2-butyn-1-yl)}methanimidamidyl]cystamine, or an acid addition salt thereof.

In another more preferred embodiment the compound of Formula IV is N,N'-bis[{N-cyano-N'-(3-butyn-1-yl)}methanimidamidyl]cystamine, or an acid addition salt thereof.

In another more preferred embodiment the compound of Formula IV is N,N'-bis[{N-cyano-N'-(4-pentyn-1-yl)}methanimidamidyl]cystamine, or an acid addition salt thereof.

In still another more preferred embodiment the compound of Formula IV is N,N'-bis[{N-cyano-N'-(2-methyl-3-butyn-2-yl)}methanimidamidyl]cystamine, or an acid addition salt thereof.

In yet another more preferred embodiment the compound of Formula IV is N,N'-bis[{N-cyano-N'-(3-butyn-2-yl)}-methanimidamidyl]cystamine, or an acid addition salt thereof.

In the most preferred embodiment the compound of Formula IV is N,N'-bis[(N-cyano-N'-propargyl)methanimidamidyl]cystamine, or an acid addition salt thereof.

The compounds of Formula IV may be prepared by reacting cystamine (VI) with an N-cyano-N'-alkynyl-S-methylisothiourea of the formula

in which $R^1$ is an defined above, in a ratio of about 2 moles of compound VII per mole of cystamine, in an inert organic solvent. Suitable inert organic solvents include, for example, (lower)alkanols, acetonitrile, DMF, DMSO, acetone and the like. We normally prefer to conduct the reaction in DMF.

The reaction temperature is not critical; the reaction may be conducted at temperatures of from about 0° to about 200°. At low temperatures the reaction is slow, while high temperatures normally lead to less pure products due to decomposition and the formation of side-products. We normally prefer to conduct the reaction at room temperature.

When reacting cystamine with an N-cyano-N'-alkynyl-S-methylisothiourea of Formula VII to produce a compound of Formula IV it has been found desirable to conduct the reaction in the presence of a small amount of hydroquinone and to bubble nitrogen through the reaction mixture. These reaction conditions were found to produce compounds of Formula IV in higher yield and of higher purity. The nitrogen sweep is believed to remove the methyl mercaptan produced in the reaction and thereby avoid secondary reactions arising from the addition of methyl mercaptan to the carbon-carbon triple bond. It is believed that the hydroquinone prevents the formation of free radicals and secondary reactions arising from their presence.

The acid addition salts of a compound of Formula IV referred to herein are intended to include salts of a compound of Formula IV with any conventional inorganic or organic acid, e.g. hydrochloric, hydrobromic, sulfuric, sulfamic, phosphoric, nitric, maleic, fumaric, succinic, oxalic, acetic, propionic, tartaric, citric, camphorsulfonic, and the like. The acid addition salts are prepared by conventional methods.

As used herein the term "(lower)alkanol" means a straight or branched chain aliphatic alcohol containing from 1 to 6 carbon atoms. The abbreviations DMF and DMSO represent dimethylformamide and dimethylsulfoxide, respectively. All temperatures herein are given in degrees centigrade. Celite is a registered trademark of the Johns-Manville Products Corporation for diatomaceous earth.

Preparation of Starting Materials

The N-cyano-N'-alkynyl-S-methylisothiourea starting materials of Formula VII utilized herein may be prepared by reacting dimethyl cyanodithioiminocarbonate with about an equimolar amount of the appropriate alkynylamine, as described in our colleagues' application Ser. No. 848,959, now U.S. Pat. No. 4,112,234. The dimethyl cyanodithioiminocarbonate which is used as a starting material for the preparation of the N-cyano-N'-alkynyl-S-methylisothioureas may itself be prepared by procedures described in J. Org. Chem., 32, 1566 (1967). The alkynylamine starting materials are either commercially available or may be prepared by methods described in Bull. Soc. Chim. Fr., 490 (1958); Bull Soc. Chim. Fr., 592 (1967) and Annales de Chimie (Paris), 3, 656 (1958).

The compounds of Formula IV may be converted to compounds of Formula III by the general procedure for the reduction of disulfides to thiols, as described by J. J. D'Amico in J. Org. Chem., 26, 3436 (1961), as shown in the following reaction scheme:

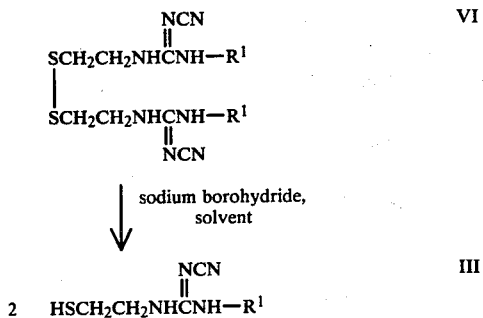

wherein R¹ is as described above.

The compounds of Formula III may subsequently be converted to the anti-ulcer agents of Formula I by the process described in our colleagues co-pending application Ser. No. 906,901, as shown in the following reaction scheme.

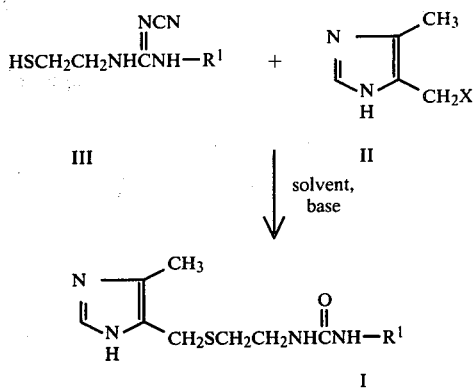

in which R¹ and X are as described above. The reduction of compounds of Formula IV to compounds of Formula III, and the subsequent reaction of compounds of Formula III with a compound of Formula II to produce anti-ulcer agents of Formula I are further described in the following Illustrative Procedures.

Illustrative Procedure 1

N-Cyano-N'-{2-[(4-methyl-5-imidazolyl)methylthio]ethyl}-N''-propargylguanidine

A.

N-Cyano-N'-propargyl-N''-(2-mercaptoethyl)guanidine

To a solution of 0.082 g (0.226 m mole) of N,N'-bis[(N-cyano-N'-propargyl)methanimidamidyl]cystamine in 4 ml ethanol was added a solution of 0.082 g sodium borohydride in 2 ml ethanol and the mixture was stirred at room temperature for 1.5 hours. Acetic acid (1 ml) was added to decompose excess borohydride, the solution was poured into an 8% solution of sodium bicarbonate in water (50 ml) and extracted with chloroform (3×15 ml). The chloroform solution, after drying (Na₂SO₄), was evaporated to dryness to give 0.056 g of the title product as a syrup. I.R. (nujol): 3410 and 3270 (NH), 2540 (SH), 2160 (C≡N), 1590 (C=N) cm⁻¹; n.m.r. (CDCl₃—CH₃OD) δ, 4.21 (NH), 4.03 (d, 2H, C$\underline{H}_2$C≡C, J=2.5 Hz), 3.43 (m, 2H, C$\underline{H}_2$N), 2.73 (m, 2H, SC$\underline{H}_2$), 2.45 (t, 1H, C≡CH, J=2.5 Hz).

This product, without further purification was used in step B.

B.

N-Cyano-N'-{2-[(4-methyl-5-imidazolyl)methylthio]ethyl}-N''-propargylguanidine

A solution of 0.029 g (0.16 m mole) of the product of step A, in 1 ml ethanol containing 0.42 m mole sodium ethoxide, was placed under a nitrogen atmosphere and cooled to 4° C. with stirring. After 5 minutes, 0.035 g (0.21 m mole) of solid 4-methyl-5-chloromethylimidazole was added. The mixture was stirred for 40 minutes, poured into brine (30 ml) and then extracted with chloroform (3×15 ml). After drying (Na₂SO₄), the solvent was removed by evaporation. The residue was purified by thin layer chromatography on silica gel plates using a methanol-chloroform (1:4) solvent system to give 0.022 g (50%) of the title compound as a syrup which crystallized on standing at room temperature. Trituration with chloroform gave the crystalline product, m.p. 147°–149° C. I.R. (nujol): 3360 (NH), 3300 (C≡CH), 2160 (C≡N), 1600 and 1585 (C=N) cm⁻¹; n.m.r. (acetone D₆): δ 8.53 (1H, NH), 7.68 (s, 1H), 7.00

(1H, NH), 4.13 (q, 2H, J=2.5 Hz), 3.73 (s, 2H), 3.53 (m, 2H), 2.73 (m, 3H), 2.21 (s, 3H).

Illustrative Procedure 2

The general procedure of Illustrative Procedure 1 is repeated except that the N,N'-bis[(N-cyano-N'-propargyl)methanimidamidyl]cystamine utilized therein is replaced by
N,N'-bis[{N-cyano-N'-(2-butyn-1-yl)}methanimidamidyl]cystamine,
N,N'-bis[{N-cyano-N'-(3-butyn-1-yl)}methanimidamidyl]cystamine,
N,N'-bis[{N-cyano-N'-(4-pentyn-1-yl)}methanimidamidyl]cystamine,
N,N'-bis[{N-cyano-N'-(2-methyl-3-butyn-2-yl)}methanimidamidyl]cystamine and
N,N'-bis[{N-cyano-N'-(3-butyn-2-yl)}methanimidamidyl]cystamine, respectively,
and there is thereby produced
N-cyano-N'-{2-[(4-methyl-5-imidazolyl)methylthio]ethyl}-N''-(2-butyn-1-yl)guanidine,
N-cyano-N'-{2-[(4-methyl-5-imidazolyl)methylthio]ethyl}-N''-(3-butyn-1-yl)guanidine,
N-cyano-N'-{2-[(4-methyl-5-imidazolyl)methylthio]ethyl}-N''-(4-pentyn-1-yl)guanidine,
N-cyano-N'-{2-[(4-methyl-5-imidazolyl)methylthio]ethyl}-N''-(2-methyl-3-butyn-2-yl)guanidine and
N-cyano-N'-{2-[(4-methyl-5-imidazolyl)methylthio]ethyl}-N''-(3-butyn-2-yl)guanidine, respectively.

This invention is illustrated by, but in no way limited to, the following Examples.

EXAMPLE 1

N,N'-bis[(N-Cyano-N'-propargyl)methanimidamidyl]cystamine

Cystamine hydrochloride (2.25 g, 10 m moles) (Aldrich Chemical Co. Ltd) was treated with 1 N aqueous sodium hydroxide (20 ml) to liberate the base and then evaporated to dryness. The residue was stirred with 2-propanol and the suspension filtered through a bed of Celite filter aid to remove the inorganic salts. The filtrate was evaporated to dryness to give cystamine free base as an oil. This oil was dissolved in 5 ml DMF and added to a solution of 3.06 g (20 m moles) of N-cyano-N'-propargyl-S-methylisothiourea and 0.11 g hydroquinone in 5 ml DMF, and the reaction mixture was allowed to stand at room temperature for 16 hours while nitrogen was bubbled through the solution. The reaction mixture was diluted with ethyl acetate saturated with water (150 ml) and washed first with water saturated with ethyl acetate (2×100 ml) and then with brine (100 ml). After drying over sodium sulfate, the solvent was removed by evaporation. The solid residue was triturated with carbon tetrachloride (50 ml), filtered and washed with carbon tetrachloride (50 ml) to give 2.68 g of the title product, m.p. 134°-136° C. Extraction of the sodium sulfate drying agent with methanol (150 ml) afforded an additional 0.41 g of the title product, thus increasing the yield to 3.09 g (85.5%). I.R. (nujol), 3290 (C≡CH), 3270 (NH), 2160 (C≡N), 1595 and 1580 (C=N) cm$^{-1}$; n.m.r. (CD$_3$OD): δ, 4.00 (d, 4H, N—$\underline{CH_2}$C≡CH, J=2.6 Hz), 3.60 (m, 4H, $\underline{CH_2}$N), 2.90 (m, 4H, —$\underline{SCH_2}$—), 2.66 (t, 2H, C≡CH, J=2.5 Hz).

Anal. Calc'd for C$_{14}$H$_{18}$N$_8$S$_2$: C, 46.38; H, 5.00; N, 30.91; S, 17.69. Found: C, 46.12; H, 4.91; N, 31.21; S, 17.41.

EXAMPLE 2

N,N'-bis[{N-Cyano-N'-(2-butyn-1-yl)}methanimidamidyl]cystamine

The general procedure of Example 1 is repeated except that the N-cyano-N'-propargyl-S-methylisothiourea utilized therein is replaced by an equimolar amount of N-cyano-N'-(2-butyn-1-yl)-S-methylisothiourea, and the title product is thereby produced.

EXAMPLE 3

N,N'-bis[{N-Cyano-N'-(3-butyn-1-yl)}methanimidamidyl]cystamine

The general procedure of Example 1 is repeated except that the N-cyano-N'-propargyl-S-methylisothiourea utilized therein is replaced by an equimolar amount of N-cyano-N'-(3-butyn-1-yl)-S-methylisothiourea, and the title product is thereby produced.

EXAMPLE 4

N,N'-bis[{N-Cyano-N'-(4-pentyn-1-yl)}methanimidamidyl]cystamine

The general procedure of Example 1 is repeated except that the N-cyano-N'-propargyl-S-methylisothiourea utilized therein is replaced by an equimolar amount of N-cyano-N'-(4-pentyn-1-yl)-S-methylisothiourea, and the title product is thereby produced.

EXAMPLE 5

N,N'-bis[{N-Cyano-N'-(2-methyl-3-butyn-2-yl)}methanimidamidyl]cystamine

The general procedure of Example 1 is repeated except that the N-cyano-N'-propargyl-S-methylisothiourea utilized therein is replaced by an equimolar amount of N-cyano-N'-[(2-methyl-3-butyn-2-yl)methanimidamidyl]cystamine, and the title product is thereby produced.

EXAMPLE 6

N,N'-bis[{Cyano-N'-(3-butyn-2-yl)}methanimidamidyl]cystamine

The general procedure of Example 1 is repeated except that the N-cyano-N'-propargyl-S-methylisothiourea utilized therein is replaced by an equimolar amount of N-cyano-N'-(3-butyn-2-yl)-S-methylisothiourea, and the title product is thereby produced.

We claim:

1. A compound of the formula

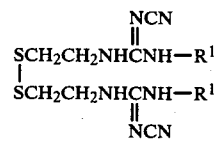

in which each R$^1$ is the same and is a straight or branched chain alkynyl group containing from 3 to 9 carbon atoms, or an acid addition salt thereof.

2. A compound of claim 1 having the formula

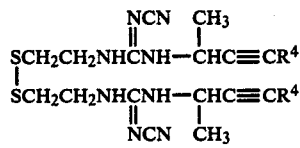

wherein each $R^4$ is the same and is hydrogen or methyl, or an acid addition salt thereof.

3. A compound of claim 1 having the formula

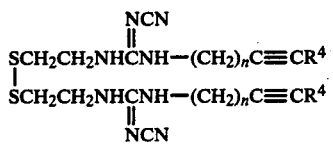

wherein each $R^4$ is the same and is hydrogen or methyl, and n is an integer of from 1 to 6 inclusive, or an acid addition salt thereof.

4. A compound of claim 1 having the formula

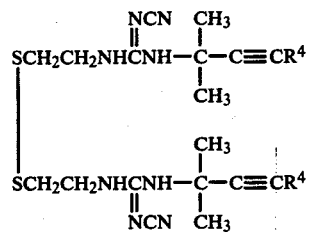

wherein each $R^4$ is the same and is hydrogen or methyl, or an acid addition salt thereof.

5. The compound of the formula

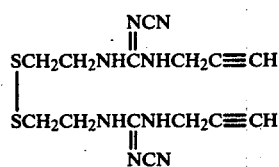

or an acid addition salt thereof.

6. The compound of the formula

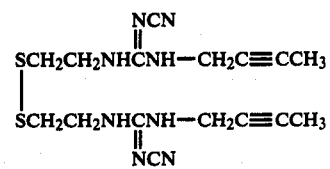

or an acid addition salt thereof.

7. The compound of the formula

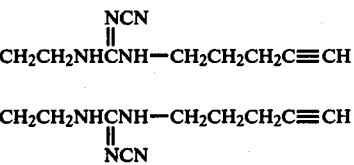

or an acid addition salt thereof.

8. The compound of the formula

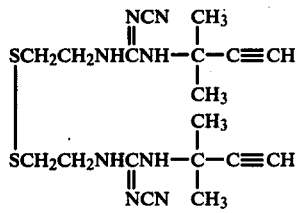

or an acid addition salt thereof.

9. The compound of the formula

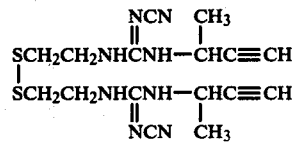

or an acid addition salt thereof.

10. The compound of the formula $$\begin{array}{c} \text{NCN} \quad \text{CH}_3 \\ \| \quad | \\ \text{SCH}_2\text{CH}_2\text{NHCNH}-\text{CHC}\equiv\text{CH} \\ | \\ \text{SCH}_2\text{CH}_2\text{NHCNH}-\text{CHC}\equiv\text{CH} \\ \| \quad | \\ \text{NCN} \quad \text{CH}_3 \end{array}$$

or an acid addition salt thereof.

* * * * *

UNITED STATES PATENT AND TRADEMARK OFFICE
CERTIFICATE OF CORRECTION

PATENT NO. : 4,157,340

DATED : June 5, 1979

INVENTOR(S) : Ronnie R. Crenshaw, Gerry Kavadias and Roger F. Saintonge

It is certified that error appears in the above-identified patent and that said Letters Patent are hereby corrected as shown below:

In column 6, line 12, the structural formula shown as

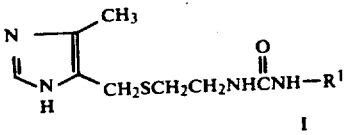

should be shown as

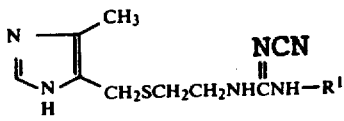

On the title page, item [73], the assignee should read -- Bristol-Myers Company --.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks